United States Patent
Fakhroo et al.

(10) Patent No.: US 11,110,172 B2
(45) Date of Patent: Sep. 7, 2021

(54) METHOD FOR TREATING MULTILOCULATED HYDROCEPHALUS BY ADMINISTERING AN ANTI-IL6 RECEPTOR ANTIBODY

(71) Applicant: IMAM ABDULRAHMAN BIN FAISAL UNIVERSITY, Dammam (SA)

(72) Inventors: Fatima AbdulRahim Fakhroo, Dammam (SA); Ahmed Ammar, Dammam (SA)

(73) Assignee: IMAM ABDULRAHMAN BIN FAISAL UNIVERSITY, Dammam (SA)

( * ) Notice: Subject to any disclaimer, the term of this patent is extended or adjusted under 35 U.S.C. 154(b) by 158 days.

(21) Appl. No.: 15/483,231

(22) Filed: Apr. 10, 2017

(65) Prior Publication Data
US 2017/0291950 A1  Oct. 12, 2017

Related U.S. Application Data

(60) Provisional application No. 62/320,119, filed on Apr. 8, 2016.

(51) Int. Cl.
*A61K 45/06* (2006.01)
*C07K 16/24* (2006.01)

(52) U.S. Cl.
CPC ............ *A61K 45/06* (2013.01); *C07K 16/248* (2013.01)

(58) Field of Classification Search
CPC ............................ C07K 16/248; A61K 45/06
See application file for complete search history.

(56) References Cited

U.S. PATENT DOCUMENTS

| | | |
|---|---|---|
| 2006/0281130 A1 | 12/2006 | Bock et al. |
| 2013/0196906 A1 | 8/2013 | Eliasof |
| 2015/0087671 A1 | 3/2015 | McClain et al. |

FOREIGN PATENT DOCUMENTS

WO  2014/018932  1/2014

OTHER PUBLICATIONS

Fakhroo et al., Targeting the IL-6/STAT3 signaling pathway by anti-IL-6 receptor antibody (Tocilizumab) in the treatment of multiloculated hydrocephalus. J. Neurol. Exp. Neural. Sci. vol. 2016, Issue 04, pp. 1-5, Dec. 2016.*
Dale, Interleukin-6 blockade as rescue therapy in autoimmune encephalitis. Neurotherapeutics, 13 (4):821-823, Oct. 2016.*
Sosvorova et al., Selected pro- and anti-inflammatory cytokines in cerebrospinal fluid in normal pressure hydrocephalus. Neuroendocrinology Letters 35 (7):586-593, 2014.*
Li et al., Formononetin protects TBI rats against neurological lesions and theunderlying mechanism. J. Neurol. Sci. 338(1-2):112-117, 2014.*
Tanaka et al. .Targeting Interleukin-6: All the Way to Treat Autoimmune and Inflammatory Diseases. International Journal of Biological Sciences 8(9):1227-1236, 2012.*
Killer et al., Cytokine and Growth Factor Concentration in Cerebrospinal Fluid from Patients with Hydrocephalus Following Endovascular Embolization of Unruptured Aneurysms in Comparison with Other Types of Hydrocephalus. Neurochem Res 35:1652-1658, 2010.*
Ersin Aslan, The effect of Tocilizumab in Experimental Alzheimer's Model. May 12, 2014.*
Sosvorova L et al., "Selected pro- and anti-inflammatory cytokines in cerebrospinal fluid in normal pressure hydrocephalus," Neuro Endocrinol Lett., 2014, vol. 35, No. 7.
Antonio Vitale et al., "Biological Treatments: New Weapons in the Management of Monogenic Autoinflammatory Disorders," Mediator of Inflammation, 2013.

* cited by examiner

*Primary Examiner* — Ruixiang Li
(74) *Attorney, Agent, or Firm* — Oblon, McClelland, Maier & Neustadt, L.L.P.

(57) ABSTRACT

The invention is directed to a method of treating multiloculated hydrocephalus comprising administering to a subject who is suffering from multiloculated hydrocephalus an antibody that binds to an IL-6 receptor.

10 Claims, No Drawings

METHOD FOR TREATING MULTILOCULATED HYDROCEPHALUS BY ADMINISTERING AN ANTI-IL6 RECEPTOR ANTIBODY

CROSS-REFERENCE TO RELATED APPLICATION

This application claims priority to U.S. Provisional Application No. 62/320,119, filed Apr. 8, 2016 which is incorporated by reference in its entirety.

BACKGROUND

Field of the Invention

The invention pertains to the fields of medicine and immunology, more specifically to treatment of multiloculated hydrocephalus by administering an antibody to IL-6 receptor or by modulating the IL-6/STAT3 pathway. Interleukin 6 (IL-6) is an inflammatory cytokine. STAT3 or "signal transducer and activator of transcription 3" is a transcription factor which in humans is encoded by the STAT3 gene.

Description of Related Art

The "background" description provided herein is for the purpose of generally presenting the context of the disclosure. Work of the presently named inventor(s), to the extent it is described in this background section, as well as aspects of the description which may not otherwise qualify as prior art at the time of filing, are neither expressly or impliedly admitted as prior art against the present invention.

Hydrocephalus (also called water on the brain) is a condition in which there is an abnormal accumulation of cerebrospinal fluid (CSF) within the brain. This typically causes increased pressure inside the skull. Older people may manifest headaches, double vision, poor balance, urinary incontinence, personality changes, or mental impairment. In babies there may be a rapid increase in head size. Other symptoms may include vomiting, sleepiness, seizures, and downward pointing of the eyes.

Hydrocephalus also manifests as a congenital birth defect or as a result of brain injury, tumor or infection that causes too much cerebrospinal fluid ("CSF") to build up in and around a baby's brain, which increases pressure on the brain problems with vision, balance or thinking as well as pain. Without surgery hydrocephalus can cause permanent brain damage. To manage this condition pediatric neurosurgeons can surgically insert a flexible plastic tube, called a brain shunt, to drain excess fluid away from the brain permitting babies with hydrocephalus to live long and healthy lives.

Loculated hydrocephalus is a condition in which discrete fluid-filled compartments form in or in relation to the ventricular system of the brain. Both uni- and multiloculated variants exist, with marked differences in outcome. Several competing and seemingly interchangeable nomenclatures exist, but none address the pathophysiological basis of the condition.

Multiloculated hydrocephalus is characterized by progressive proliferation of multiple intraventricular septations, resulting in multiple cystic cavities in the ventricles. Surgical management is performed neuroendoscopically by creating fenestration between the cavities to decrease the number of shunts used. However, intraventricular septations continue to proliferate requiring multiple revision surgeries. Multiple surgical interventions are associated with increased morbidity and mortality.

The etiology and pathogenesis of, and risk of developing, multiloculated hydrocephalus are associated with inflammatory processes which may be associated with either infections or chemical agents. It is triggered by insults to the central nervous system such as meningitis, including bacterial meningitis, intraventricular hemorrhage, shunt-related infections, overdrainage, direct ependymal trauma during catheter insertion, and intracranial surgery: see Eshra, Mohammed A.: Endoscopic management of septated, multiloculated hydrocephalus; Alexandria Journal of Medicine (2014) 50, 123-126; and Spennato, P., et al.: Multiloculated Hydrocephalus; Pediatric Hydrocephalus; 2004; DOI: 10.1007/978-88-470-2121-1_16, each incorporated herein by reference in their entirety.

Meningitis and intraventricular hemorrhage account for most cases. An inflammatory reaction will lead to ventriculitis which reactivates fetal mechanisms of germinal matrix glial cell proliferation and migration. Furthermore, inflammation of the ependymal stimulates proliferation of subependymal glial tissues; see Gandhoke, Gurpreet S.: Role of magnetic resonance Ventriculography in multiloculated hydrocephalus; J Neurosurg Pediatrics; 11:697-703, 2013, incorporated herein by reference in its entirety.

In addition, destruction of ependymal cells triggers the onset of septa formation by allowing the proliferating glial tissues to project into the ventricles. This forms a nidus for the formation of septations that span the ventricles and obstruct vital foramina and CSF passages; see Spennato, Pietro et al.: Neuroendoscopic treatment of multiloculated hydrocephalus in children; J Neurosurg (1 Suppl Pediatrics); 106:29-35, 2007; and Spennato, P. et al. (2004) supra., each incorporated herein by reference in their entirety.

Intraventricular septations are also formed by the accumulation of inflammatory exudates and debris on the glial projections forming isolated compartments in the ventricular system. Following ventriculitis, it takes ventricular septations an average of 2-4 months to form. As a result, the anatomy of the ventricular system will change and the normal flow of cerebrospinal fluid will be altered leading to the accumulation of cerebrospinal fluid within a loculated cavity; resulting in obstructive hydrocephalus with progressive dilatation and mass effect on the adjacent parts of the brain.

Microscopically the septations are membranes composed of fibroglial tissues and round and polymorphonuclear cells, see Spennato, P. et al. (2004), supra. The features of chronic ventriculities usually present in the form of subependymal gliosis and glial tufts extending through the destructed ependyma into the ventricular lumen.

Multiloculated hydrocephalus is one of the most challenging diseases in neurosurgery. Until now there was no definitive curative treatment because the disease is considered to be of a progressive type. As mentioned above, hydrocephalus is defined as accumulation of CSF in the ventricles which leads to increased ventricular pressure resulting in ventricular dilatation. It can then progress compressing surrounding neural tissues leading to neurological deficits.

Multiloculated hydrocephalus is a type of hydrocephalus in which in addition to all features of hydrocephalus mentioned above, there are multiple separated cystic cavities or spaces filled with CSF, isolated by multiple intraventricular septations, located in or in relation to the ventricular system.

Historically and till the present time the only definitive treatment for multiloculated hydrocephalus was surgical. The aim of surgical treatment was to drain the ventricular cavity by shunting and to create fenestrations between adjacent compartments neuroendoscopically to open multiple compartments into a single cavity, thus decreasing the number of shunts; see Gurpreet, S. et al. (2013) supra; Spennato, Pietro et al. (2007) supra Eshra, Mohammed (2014) supra; and Andresen, Morten et al.: Multiloculated hydrocephalus a review of current problems in classification and treatment; Childs Nerv Sysr (2012) 28:357-362; DOI 10, 1007//s00381-012-1702-3, each incorporated herein by reference in their entirety.

Despite all these treatments the septations continue to proliferate leading to accumulation of CSF in isolated compartments that compress surrounding neural tissues. As a result, there is a need for 'revision surgery' later on, which is associated with increased risk of morbidity and mortality. Spennato et al. proposed that the cause behind shunt obstruction in multiloculated hydrocephalus is the chronic inflammation at ependymal level that persists for a long time and that chronic inflammation results in formation of new septa thus leading to further obstruction. Thus, multiloculated hydrocephalus was considered to be a progressive disease; see Eshra, Mohammed (2014) supra.

Until the present time there was no standard medical therapy for treating pathogenic factors associated with multiloculated hydrocephalus except to administer antibiotics that treat associated meningitis or shunt related infections. While multiple studies describe potential surgical treatments of the disease, no study proposed treating the pathophysiological factors underlying this progressive disease.

Hydrocephalus may be diagnosed using ultrasound, computed tomography (CT scan) and/or MRI scan. These scans typically reveal enlarged ventricles and may indicate a specific cause. Ultrasound imaging, which uses high-frequency sound waves to produce images, is often used for an initial assessment for infants because it's a relatively simple, low-risk procedure. The ultrasound device is placed over the soft spot (fontanel) on the top of a baby's head. Ultrasound may also detect hydrocephalus prior to birth when the procedure is used during routine prenatal examinations. Magnetic resonance imaging (MRI) uses radio waves and a magnetic field to produce detailed 3-D or cross-sectional images of the brain. This test is painless, but it is noisy and requires lying still. Some MM scans can take up to an hour and require mild sedation for children. However, some hospitals may use a quick version of MRI that takes about five minutes and doesn't require sedation. Computerized tomography (CT) scan is a specialized X-ray technology that can produce cross-sectional views of the brain. Scanning is painless and takes about 20 minutes. This test also requires lying still, so a child usually receives a mild sedative. CT scans for hydrocephalus are usually used only for emergency exams.

Reactive gliosis refers to responses of glial cells associated with central nervous system ("CNS") injury or disease. When CNS insult occurs, there is a multicellular response divided into three overlapping phases: 1) cell damage, death and inflammation, 2) cell proliferation for tissue replacement, and 3) tissue remodeling; see Burda, Joshua E. et al.: Reactive gliosis and the multicellular response to CNS Damage and Disease; Neuron review, http://dx.doi.org/10.1016/j.neuron.2013.12.034, incorporated herein by reference in its entirety.

The second and third phases are important because the proliferation of fibroblast-lineage cells, various type of glia including scar-forming astrocytes, and scar organization occur in these phases. Formation of compact astrocyte scar (glial scar) is a specialized aspect of reactive astrogliosis that occurs in response to severe tissue damage and leukocyte infiltration and involves phases of cell proliferation and cell organization. There are multiple molecules that trigger astrocyte proliferation and astrocyte scar formation. One of them is the IL-6 released by local cells and leukocytes. In addition, organization of newly proliferated astrocytes into compact scars occurs via the IL-6 receptor-STAT3 signaling system.

Interleukin 6 ("IL-6") signals through a cell-surface type I cytokine receptor complex consisting of the ligand-binding IL-6Rα chain (CD126), and the signal-transducing component gp130 (also called CD130). Gp130 is the common signal transducer for several cytokines including leukemia inhibitory factor (LIF), ciliary neurotropic factor, oncostatin M, IL-11 and cardiotrophin-1, and is ubiquitously expressed in most tissues. In contrast, the expression of CD126 is restricted to certain tissues.

IL-6 receptor (IL-6R) is a protein, with a ligand-binding IL-6 receptor chain, and a signal-transducing subunit gp130; see Kamimura, Daisuke et al. (2014) supra. However, binding of IL-6 to the IL-6R doesn't activate the signaling cascade. But, binding of the IL-6 with IL-6R associated protein gp130 forming a complex activates the intracellular signaling via JAK/STAT pathway. Furthermore, it was found that activation of the STAT pathway is the one that leads to the anti-inflammatory effect of IL-6 in the form of: 1) activation of cell proliferation, and 2) inhibition of cell apoptosis. Thus, it leads to tissue regeneration.

As IL-6 interacts with its receptor, it triggers the gp130 and IL-6R proteins to form a complex thus activating the receptor. These complexes bring together the intracellular regions of gp130 to initiate a signal transduction cascade through certain transcription factors, Janus kinases (JAKs) and Signal Transducers and Activators of Transcription (STATs); Heinrich P C, et al., "Interleukin-6-type cytokine signaling through the gp130/Jak/STAT pathway". *The Biochemical Journal.* 334 (Pt 2): 297-314 (1998).

Antibodies to IL-6 receptors are known. Tocilizumab is a humanized monoclonal antibody that recognizes IL-6 receptor; see Kang, Sujin et al.: Therapeutic uses of anti-interleukin-6 receptor antibody; International Immunology, Vol. 27, No. 1, pp. 21-29, 2014; DOI:10.1093/intimm/dxu081, incorporated herein by reference in its entirety.

It can block all signaling pathways of IL-6 by inhibiting the binding of IL-6 to IL-6R. Tocilizumab was proved clinically to be effective in the treatment of various diseases and significantly reduced the inflammation associated with rheumatoid arthritis and systemic juvenile arthritis; see Choy, E. H. et al. 2002. Therapeutic benefit of blocking interleukin-6 activity with an anti-interleukin-6 receptor monoclonal antibody in rheumatoid arthritis: a randomized, double-blind, placebo-controlled, dose-escalation trial. Arthritis Rheum. 46:3143; Nishimoto, N. et al. 2004. Treatment of rheumatoid arthritis with humanized anti-interleukin-6 receptor antibody: a multicenter, double-blind, placebo-controlled trial. Arthritis Rheum. 50:1761; Tanaka, T. et al. 2014. Monoclonal antibodies in rheumatoid arthritis: comparative effectiveness of tocilizumab with tumor necrosis factor inhibitors. Biologics 8:141; Yokota, S. et al. 2008. Efficacy and safety of tocilizumab in patients with systemic-onset juvenile idiopathic arthritis: a randomized, double-blind, placebo-controlled, withdrawal phase III trial. Lancet 371:998; and De Benedetti, F. et al.; PRINTO; PRCSG. 2012. Randomized trial of tocilizumab in systemic juvenile idiopathic arthritis. N. Engl. J. Med. 367:2385, each incorporated herein by reference in their entirety.

Studies also have been done to test the use of Tocilizumab in the treatment of some kinds of cancers since they showed increased level of IL-6 with activation of the STAT3 signaling pathway in order to inhibit the tumorigenesis and to suppress aggressive inflammatory cancers; see Sansone, Pasquale et al: Targeting the Interleukin-6/Jak/Stat Pathway in Human Malignancies; J Clin Oncol 30:1005-1014, 2012; DOI: 10.1200/JCO.2010.31.8907; Liu, Yan et al.: Inhibition of STAT3 signaling blocks the anti-apoptotic activity of IL-6 in human liver cancer cells. THE JOURNAL OF BIOLOGICAL CHEMISTRY VOL. 285, NO. 35, pp. 27429-27439, Aug. 27, 2010; DOI 10.1074/jbc.M110.142752; Osuala, Kingsley O. et al.: I1-6 signaling between ductal carcinoma in situ cells and carcinoma-associated fibroblasts mediates tumor cell growth and migration; Osuala et al. BMC Cancer (2015) 15:584; DOI 10.1186/s12885-015-1576-3, each incorporated herein by reference in their entirety.

The safety profile of Tocilizumab was studied on patients with rheumatoid arthritis treated with this agent; see Tanaka, T. et al. (2010) Tocilizumab for the treatment of rheumatoid arthritis. Expert Rev. Clin. Immunol. 6, 843-854, incorporated herein by reference in its entirety. The most common side effects are: upper respiratory tract infection, nasopharyngitis, headache, and hypertension. See Tanaka, Toshio et al.: Anti-interleukin-6 receptor antibody, tocilizumab, for the treatment of autoimmune diseases; FEBS Letters 585 (2011) 3699-3709, incorporated herein by reference in its entirety. The severe life threatening side effects are: serious infections, gastrointestinal perforations, and hypersensitivity reactions including anaphylaxis. On the other hand, there is no increased incidence of malignancy, tuberculosis activation, or hepatitis.

Interleukin-6 (IL-6) is a multifunctional cytokine protein. See Kamimura, Daisuke et al.: IL-6 and inflammatory diseases; Springer Japan 2014; DOI 10.1007/978-4-431-54442-5_2, incorporated herein by reference in its entirety. It has a role in inflammation and infection responses, regulation of immune system, neural processes, and promotion of tumorigenesis. See Kamimura, Daisuke et al. supra.; Scheller, Jürgen et al.: The pro- and anti-inflammatory properties of the cytokine interleukin-6; Biochimica et Biophysica Acta; 1813 (2011) 878-888; Rose-John, Stefan: IL-6 trans-signaling via the soluble IL-6 receptor importance for the pro-inflammatory activities of IL-6; Int J. Biol. Sci. 2012; 8(9):1237-1247; doi: 10.7150/ijbs.4989; Kojima, Hirotada et al.: IL-6-STAT3 signaling and premature senescence; JAKSTAT 2:4, e2576, 2013, each incorporated herein by reference in their entirety. Also, IL-6 was found to be elevated in a number of diseases: infections, autoimmune diseases, some solid cancers, neurological diseases, and tissue aging; see Griesinger, Andrea M. et al.: Interleukin-6/STAT3 pathway signaling drives an inflammatory phenotype in group A ependymoma; Cancer Immunol Res 2015; 3:1165-1174; doi:10.1158/2326-6066.CIR-15-0061; Rose-John, Stefan (2012) supra.; Kojima, Hirotada et al. (2013) supra.; and Kang, Sujin et al. (2014) supra.; each incorporated herein by reference in their entirety.

IL-6 was found to be elevated in a number of CNS conditions; infection, inflammation, and malignancy. A study done to identify the relationship between the cytokines in the plasma and CSF, showed that ventriculostomy-related infection was associated with CSF IL-6>10,000 pg/ml (P value highly significant). See Hopkins, Stephen J. et al.: Cerebrospinal fluid and plasma cytokines after subarachnoid haemorrhage CSF interleukin-6 may be an early marker of infection; Journal of Neuroinflammation 2012 9:255; DOI: 10:1186/1742-2094-9-255, incorporated herein by reference in its entirety. The study concluded that infection had important influence on cytokine production especially IL-6 and that measurements of IL-6 in CSF can be used as maker for ventriculostomy-related injections. Furthermore, a study was conducted on patients with sporadic amyotrophic lateral sclerosis which is CNS inflammation with infiltration of inflammatory cells in the spinal cord; see Fiala, Milan et al.: Tocilizumab infusion therapy normalizes inflammation in sporadic ALS patients; Am J Neurodegener Dis 2013; 2(2): 129-139, incorporated herein by reference in its entirety. Tocilizumab infusion was given to the subject. Results supported research hypothesis that Tocilizumab infusions may benefit these patients by normalizing IL-6 expression. Finally, ependymoma is a childhood brain tumor with poor prognosis. Ependymoma group A is an aggressive type, and studying its molecular level revealed an inflammatory response; see Griesinger, Andrea M. et al. (2015) supra. Also, IL-6 and STAT3 pathway genes enriched ependymoma group A, indicating activation of IL-6/STAT3 mechanism in this group which is responsible for the inflammation. In addition, ependymoma cell growth was shown to be dependent on IL6/STAT3 pathway, because pharmacological inhibition of STAT3 resulted in blocking proliferation and inducing apoptosis.

STAT3 is a member of the STAT protein family. In response to cytokines and growth factors STAT3 is phosphorylated by receptor-associated Janus kinases (JAK), form homo- or heterodimers, and translocate to the cell nucleus where they act as transcription activators. Specifically, STAT3 becomes activated after phosphorylation of tyrosine 705 in response to such ligands as interferons, epidermal growth factor (EGF), Interleukin IL-5 and IL-6.

Additionally, activation of STAT3 may occur via phosphorylation of serine 727 by Mitogen-activated protein kinases (MAPK), Tkach M, et al. "p42/p44 MAPK-mediated Stat3 Ser727 phosphorylation is required for progestin-induced full activation of Stat3 and breast cancer growth". Endocrine-related cancer. 20 (2): 197-212 (2013); and through c-src non-receptor tyrosine kinase; Silva C M, "Role of STATs as downstream signal transducers in Src family kinase-mediated tumorigenesis". Oncogene. 23 (48): 8017-802 (2004) and Lim C P, et al., "Structure, function, and regulation of STAT proteins". Molecular BioSystems. 2 (11): 536-550 (2006). STAT3 mediates the expression of a variety of genes in response to cell stimuli, and thus plays a key role in many cellular processes such as cell growth and apoptosis' Yuan Z L, et al., "Central role of the threonine residue within the p+1 loop of receptor tyrosine kinase in STAT3 constitutive phosphorylation in metastatic cancer cells". Molecular and Cellular Biology. 24 (21): 9390-9400 (2004).

BRIEF SUMMARY OF THE INVENTION

The invention is directed to a method of treating multiloculated hydrocephalus comprising administering to a subject who is suffering from multiloculated hydrocephalus an antibody that binds to an IL-6 receptor. Advantageously, this method may be used to treat subjects at risk of developing multiloculated hydrocephalus, subjects who have multiloculated hydrocephalus or those who are at risk of progression of multiloculated hydrocephalus. Multiloculated hydrocephalus is caused by progressive proliferation of multiple intraventricular septations resulting in multiple cystic cavities in the ventricles. Surgical management is neuroendoscopically by creating fenestrations between cavities to decreases the number of shunts used. However, this disease is progressive and intraventricular septations continue to proliferate usually requiring multiple revision surgeries. These revision surgeries increase morbidity and mortality. In contrast to prior modes of surgical treatment, the invention provides a way to inhibit IL-6 induced proliferation of brain cells as a way to mitigate the pathophysiology and underlying biochemical changes associated with multiloculated hydrocephalus.

DETAILED DESCRIPTION OF THE INVENTION

The inventors describe a new medical treatment in the form of agents targeting the underlying pathophysiology of the progressive nature of septa formation in multiloculated hydrocephalus. This treatment can be used as a primary treatment or as an adjuvant treatment to prevent further septa formation. Progressive proliferation of intraventricular septations in multiloculated hydrocephalus is associated with chronic inflammatory process and activation of IL-6/STAT3 signaling pathway. While not being bound to any particular theory or mechanism the inventors believe that anti-IL-6 receptor antibodies, such as Tocilizumab, and other STAT3 pathway inhibitors, treat multiloculated hydrocephalus by suppressing glial and other brain cell proliferation thus preventing or inhibiting chronic ventriculitis and formation or progression of intraventricular septations.

Progressive septa formation is associated with inflammatory processes and their sequelae. While there are no studies about the cellular and molecular basis of multiloculated hydrocephalus, there is evidence that underlying cause of progressive intraventricular septations is ventriculitis; see Spennato, P. et al. (2004) supra. Ventriculostomy-related infection was associated with IL-6 levels in the CSF>10,000 pg/ml which is significant; see Hopkins, Stephen J. et al. (2012) supra. Also, IL-6 activation of the STAT3 in response to CNS insult is a signaling pathway that triggers astrocyte proliferation and astrocyte scar formation; see Burda, Joshua E. et al.: Reactive gliosis and the multicellular response to CNS Damage and Disease; Neuron review. http://dx.doi.org/10.1016/j.neuron.2013.12.034, incorporated herein by reference in its entirety.

The inventors investigated whether an etiological factor of multiloculated hydrocephalus initiates an inflammatory response that persists and elevates IL-6 level in CSF, activating IL-6/STAT3 signaling pathway. During chronic inflammation ependymal cells lining the ventricle are exposed to elevated levels of cytokines, specifically IL-6, which could cause progressive formation of intraventricular septations through IL-6/STAT3 which promotes cell proliferation astrocytes', inhibit apoptosis, and organize compact astrocyte scar. To reduce inflammation and prevent or ameliorate intraventricular septa formation associated with multiloculated hydrocephalus, the inventors studied the effects of antibodies that inhibit IL-6 activity, such as the IL-6 receptor antibody (Tocilizumab).

Tocilizumab is a humanized monoclonal antibody that blocks signaling pathways by inhibiting the binding of IL-6 to IL-6R, has been proved by the FDA for the treatment of some inflammatory diseases associated with increased levels of IL-6 and other cytokines like rheumatoid arthritis and systemic juvenile arthritis; see Kang, Sujin et al. (2014) supra. This agent decreased the inflammation associated with these diseases, maintained disease remission, and slowed the progression of disease manifestation. Moreover, trial studies have been carried out for using Tocilizumab in CNS diseases associated with inflammation and elevated levels of IL-6 like in sporadic amyotrophic lateral sclerosis and ependymoma. These studies showed that Tocilizumab normalized IL-6 levels and suppressed inflammation. Also, in ependymoma inhibition of the IL-6/STAT3 pathway blocked cell proliferation and induced apoptosis.

Based on these studies, the inventors believe that multiloculated hydrocephalus is a chronic inflammatory disease with progressive growth of intraventricular septations associated with gliosis and that agents such as Tocilizumab can stop progressive intraventricular septations by blocking IL-6/STAT3 signaling pathway which is responsible for the astrocyte 'glial' scar formation.

Results described below show that elevated levels of IL-6 cause whole brain cell proliferation. Thus, inhibition of such proliferation using IL-6 antagonists such as antibodies to IL-6 receptor or STAT3 inhibitors could treat brain diseases or disorders associated with cellular proliferation.

The invention is described by reference to the following definitions and features. Various embodiments of the invention may incorporate one or more features, elements, ranges or alternatives described below.

The term "antibody" or "immunoglobulin," as used interchangeably herein, includes whole antibodies and any antigen binding fragment (antigen-binding portion) or single chain cognates thereof. For example, it encompasses intact or full length antibodies binding to IL-6 receptor, fragments of such antibodies that bind to IL-6 receptor, as well as modified antibodies, antibody complex or conjugates that bind to IL-6 receptors.

An "antibody" comprises at least one heavy (H) chain and one light (L) chain. In naturally occurring IgGs, for example, these heavy and light chains are inter-connected by disulfide bonds and there are two paired heavy and light chains, these two also inter-connected by disulfide bonds. Each heavy chain contains a heavy chain variable region (abbreviated herein as $V_H$) and a heavy chain constant region. The heavy chain constant region contains three domains, CH1, CH2 and CH3. Each light chain contains a light chain variable region (abbreviated herein as $V_L$) and a light chain constant region. The light chain constant region contains one domain, CL. The $V_H$ and $V_L$ regions can be further subdivided into regions of hypervariability, termed complementarity determining regions (CDR), interspersed with regions that are more conserved, termed framework regions (FR) or Joining (J) regions (JH or JL in heavy and light chains respectively). Each $V_H$ and $V_L$ is composed of three CDRs three FRs and a J domain, arranged from amino-terminus to carboxy-terminus in the following order: FR1, CDR1, FR2, CDR2, FR3, CDR3, and J. The variable regions of the heavy and light chains bind with an antigen. The constant regions of the antibodies may mediate the binding of the immunoglobulin to host tissues or factors, including various cells of the immune system (e.g., effector cells) or humoral factors such as the first component (Clq) of the classical complement system. Thus one or more fragments of an antibody that retain the ability to specifically bind to an antigen (e.g., IL-6 receptor or IL-6) may be used in the combinations disclosed herein. It has been shown that fragments of a full-length antibody can perform the antigen-binding function of an antibody. Examples of binding fragments denoted as an antigen-binding portion or fragment of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb including $V_H$ and $V_L$ domains; (vi) a dAb fragment (Ward et al. (1989) Nature 341, 544-546), which consists of a $V_H$ domain; (vii) a dAb which consists of a $V_H$ or a $V_L$ domain; and (viii) an isolated complementarity determining region (CDR) or (ix) a combination of two or more isolated CDRs which may optionally be joined by a synthetic linker. Furthermore, although the two domains of the Fv fragment, $V_H$ and $V_L$, are coded for by separate genes, they can be joined, using recombinant methods, by a synthetic linker that enables them to be made as a single protein chain in which the $V_H$ and $V_L$ regions are paired to form monovalent molecules (such as single chain cognate of an immunoglobulin fragment is known as a single chain $F_v$ (sc$F_v$). Such single chain antibodies are also intended to be encompassed within the term "antibody". Antibody fragments are obtained using conventional techniques known to those with skill in the art, and the fragments are screened for utility in the same general manner as are intact antibodies. Antigen-binding portions can be produced by recombinant DNA techniques, or by enzymatic or chemical cleavage of intact immunoglobulins.

An antibody may be polyclonal or monoclonal and of any class or isotype, such as IgG1, IgG2, IgG3, IgG4, IgM, IgA1, IgA2, s-IgA, IgD and IgE. IL-6 receptor binding or IL-6 binding antibodies, antibody fragments, such as Fv, Fab, Fab'2, or ScFv, modified antibodies, bispecific antibodies, intrabodies, nanobodies, antibody mimetics, small molecules or peptides, or antibody conjugates, may be employed in some embodiments of the invention.

The term "monoclonal antibody" as used herein refers to an antibody obtained from a population of substantially homogeneous antibodies, i.e., the individual antibodies comprising the population are identical except for possible naturally occurring mutations that may be present in minor amounts. Antigen binding fragments (including sc$F_v$s) of such immunoglobulins are also encompassed by the term "monoclonal antibody" as used herein. Monoclonal antibodies (mAb or moAb) are antibodies that are made by identical immune cells that are all clones of a unique parent cell. Monoclonal antibodies can have monovalent affinity, in that they bind to the same epitope (the part of an antigen that is recognized by the antibody). In contrast, polyclonal antibodies bind to multiple epitopes and are usually made by several different plasma cell (antibody secreting immune cell) lineages. Bispecific monoclonal antibodies can also be engineered, by increasing the therapeutic targets of one single monoclonal antibody to two epitopes.

Monoclonal antibodies can be prepared using any art recognized technique and those described herein such as, for example, a hybridoma method, a transgenic animal, recombinant DNA methods (see, e.g., U.S. Pat. No. 4,816,567), or using phage antibody libraries using the techniques described in, for example, U.S. Pat. No. 7,388,088 and WO/2000/031246 which are incorporated by reference. Monoclonal antibodies include chimeric antibodies, human antibodies and humanized antibodies and may occur naturally or be produced recombinantly.

The term "recombinant antibody," refers to antibodies that are prepared, expressed, created or isolated by recombinant means, such as (a) antibodies isolated from an animal (e.g., a mouse) that is transgenic or transchromosomal for immunoglobulin genes (e.g., human immunoglobulin genes) or a hybridoma prepared therefrom, (b) antibodies isolated from a host cell transformed to express the antibody, e.g., from a transfectoma, (c) antibodies isolated from a recombinant, combinatorial antibody library (e.g., containing human antibody sequences) using phage display, and (d) antibodies prepared, expressed, created or isolated by any other means that involve splicing of immunoglobulin gene sequences (e.g., human immunoglobulin genes) to other DNA sequences. Such recombinant antibodies may have variable and constant regions derived from human germline immunoglobulin sequences. In certain embodiments, however, such recombinant human antibodies can be subjected to in vitro mutagenesis and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

The term "chimeric immunoglobulin" or antibody refers to an immunoglobulin or antibody whose variable regions derive from a first species and whose constant regions derive from a second species. Chimeric immunoglobulins or antibodies can be constructed, for example by genetic engineering, from immunoglobulin gene segments belonging to different species.

The term "human antibody" as used herein, is intended to include antibodies having variable regions in which both the framework and CDR regions are derived from human germline immunoglobulin sequences as described, for example, by Kabat et al., Sequences of proteins of Immunological Interest, Fifth Edition, U.S. Department of Health and Human Services, NIH Publication No. 91-3242 (1991). Furthermore, if the antibody contains a constant region, the constant region also is derived from human germline immunoglobulin sequences. The human antibodies may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The human antibody can have at least one or more amino acids replaced with an amino acid residue, e.g., an activity enhancing amino acid residue that is not encoded by the human germline immunoglobulin sequence. Typically, the human antibody can have up to twenty positions replaced with amino acid residues that are not part of the human germline immunoglobulin sequence. In a particular embodiment, these replacements are within the CDR regions as described in detail below.

The term "humanized antibody" refers to an antibody that includes at least one humanized antibody chain (i.e., at least one humanized light or heavy chain). The term "humanized antibody chain" (i.e., a "humanized immunoglobulin light chain") refers to an antibody chain (i.e., a light or heavy chain, respectively) having a variable region that includes a variable framework region substantially from a human antibody and complementarity determining regions (CDRs) (e.g., at least one CDR, two CDRs, or three CDRs) substantially from a non-human antibody, and further includes constant regions (e.g., one constant region or portion thereof, in the case of a light chain, and preferably three constant regions in the case of a heavy chain).

As used herein, "isotype" refers to the antibody class (e.g., IgM or IgG1) that is encoded by heavy chain constant region genes. In some embodiments, a monoclonal antibody composition provided herein comprises only antibodies of the IgG1 isotype. In other embodiments, a monoclonal antibody composition provided herein comprises only antibodies of the IgG2 isotype. In other embodiments, a monoclonal antibody composition provided herein comprises antibodies of two or three different isotypes.

"Tocilizumab" (Actemra) is an FDA approved IL-6 receptor antibody for inflammatory autoimmune diseases. It is undergoing trials for use in certain CNS disorders. Prescribing and medical information regarding this product is incorporated by reference to: https://www.gene.com/download/pdf/actemra_prescribing.pdf (last accessed Apr. 5, 2017). Tocilizumab is used in some embodiments of the methods disclosed herein.

Anti-IL-6 Receptor Antibodies. In various embodiments, the IL-6 antagonist is an anti-IL-6 receptor antibody or antigen-binding fragment or derivative thereof. In some embodiments, the IL-6 antagonist is a full-length anti-IL-6 receptor monoclonal antibody. In particular embodiments, the full-length monoclonal antibody is an IgG antibody. In certain embodiments, the full-length monoclonal antibody is an IgG1, IgG2, IgG3, or IgG4 antibody. In some embodiments, the IL-6 antagonist is a polyclonal composition comprising a plurality of species of full-length anti-IL-6 receptor antibodies, each of the plurality having unique CDRs. In some embodiments, the IL-6 antagonist is an antibody fragment selected from Fab and Fab' fragments. In some embodiments, the IL-6 antagonist is a scFv, a single domain antibody, including a camelid-derived VHH single domain nanobody. In some embodiments, the antibody is bispecific or multispecific, with at least one of the antigen-binding portions having specificity for IL-6R.

In some embodiments, the antibody is fully human. In some embodiments, the antibody is humanized. In other embodiments, the antibody is chimeric and has non-human V regions and human C region domains. In some embodiments, the antibody is murine or a chimeric murine/human antibody.

In typical embodiments, the anti-IL-6 receptor antibody has a $K_D$ for binding human IL-6R of less than 100 nM. In some embodiments, the anti-IL-6R antibody has a $K_D$ for binding human IL-6R of less than 75 nM, 50 nM, 25 nM, 20 nM, 15 nM, or 10 nM. In particular embodiments, the anti-IL-6 receptor antibody has a $K_D$ for binding human IL-6R of less than 5 nM, 4 nM, 3 nM, or 2 nM. In selected embodiments, the anti-IL-6 receptor antibody has a $K_D$ for binding human IL-6R of less than 1 nM, 750 pM, or 500 pM. In specific embodiments, the anti-IL-6 receptor antibody has a $K_D$ for binding human IL-6R of no more than 500 pM, 400 pM, 300 pM, 200 pM, or 100 pM.

In typical embodiments, the anti-IL-6R antibody reduces the biological activity of IL-6 such as its ability to induce brain cell proliferation.

In typical embodiments, the anti-IL-6R antibody has an elimination half-life following intravenous administration of at least 7 days. In certain embodiments, the anti-IL-6R antibody has an elimination half-life of at least 14 days, at least 21 days, or at least 30 days.

In some embodiments, the anti-IL-6R antibody has a human IgG constant region with at least one amino acid substitution that extends serum half-life as compared to the unsubstituted human IgG constant domain.

In some embodiments, the elimination half-life of an anti-IL-6R antibody is increased by utilizing the FcRN-binding properties of human serum albumin. In certain embodiments, the antibody is conjugated to albumin; see Smith et al., Bioconjug. Chem., 12: 750-756 (2001). In some embodiments, an anti-IL-6 antibody is fused to bacterial albumin-binding domains; see Stork et al., Prot. Eng. Design Science 20: 569-76 (2007). In some embodiments, an anti-IL-6 antibody is fused to an albumin-binding peptide (Nguygen et al., Prot Eng Design Sel 19: 291-297 (2006)). In some embodiments, an anti-IL-antibody is bispecific, with one specificity being to IL-6R, and one specificity being to human serum albumin, see Ablynx, WO 2006/122825 (bispecific Nanobody).

In some embodiments, the elimination half-life of ananti-IL-6R antibody is increased by PEGylation; see Melmed et al., Nature Reviews Drug Discovery 7: 641-642 (2008); by HPMA copolymer conjugation; see Lu et al., Nature Biotechnology 17: 1101-1104 (1999); by dextran conjugation; see Nuclear Medicine Communications, 16: 362-369 (1995); by conjugation with homo-amino-acid polymers (HAPs; HAPylation); see Schlapschy et al., Prot Eng Design Sel 20: 273-284 (2007)); or by polysialylation; see Constantinou et al., Bioconjug. Chem. 20: 924-931(2009).

In certain embodiments, an anti-IL-6R antibody or antigen-binding portion thereof comprises all six CDRs of tocilizumab. In particular embodiments, the antibody or antigen-binding portion thereof comprises the tocilizumab heavy chain V region and light chain V region. In specific embodiments, the antibody is the full-length tocilizumab antibody.

In certain embodiments, the anti-IL-6R antibody or antigen-binding portion thereof comprises all six CDRs of sarilumab. In particular embodiments, the antibody or antigen-binding portion thereof comprises the sarilumab heavy chain V region and light chain V region. In specific embodiments, the antibody is the full-length sarilumab antibody.

In certain embodiments, the anti-IL-6R antibody or antigen-binding portion thereof comprises all six CDRs of VX30 (Vaccinex), ARGX-109 (arGEN-X), FM101 (Formatech), SA237 (Roche), NI-1201 (NovImmune), or an antibody described by Lee, et al. in US 2012/0225060. In other embodiments, the anti-IL-6R antibody or antigen-binding portion thereof is a single domain antibody. In particular embodiments, the single domain antibody is a camelid VHH single domain antibody. In specific embodiments, the antibody is vobarilizumab (ALX-0061) (Ablynx NV).

Anti-IL-6:IL-6R Complex Antibodies. In various embodiments, the IL-6 antagonist is an antibody specific for the complex of IL-6 and IL-6R. In certain embodiments, the antibody has the six CDRs of an antibody selected from those described by Kakkar, et al. in U.S. 2011/0002936, which is incorporated herein by reference in its entirety.

JAK and STAT Inhibitors. IL-6 is known to signal via the JAK-STAT pathway. In various embodiments, anIL-6 antagonist is an inhibitor of the JAK signaling pathway. In some embodiments, the JAK inhibitor is a JAK1-specific inhibitor. In some embodiments, the JAK inhibitor is a JAK3-specific inhibitor. In some embodiments, the JAK inhibitor is a pan-JAK inhibitor.

In certain embodiments, the JAK inhibitor is selected from the group consisting of tofacitinib (Xeljanz), decemotinib, ruxolitinib, upadacitinib, baricitinib, filgotinib, lestaurtinib, pacritinib, peficitinib, INCB-039110, ABT-494, INCB-047986 and AC-410.

In various embodiments, the IL-6 antagonist is a STAT3 inhibitor. In a specific embodiment, the inhibitor is AZD9150 (AstraZeneca, Isis Pharmaceuticals), a STAT3 antisense molecule.

Other IL-6 Antagonists. In various embodiments, the IL-6 antagonist is an antagonist peptide. In certain embodiments, the IL-6 antagonist is C326 (an IL-6 inhibitor by Avidia, also known as AMG220), or FE301, a recombinant protein inhibitor of IL-6 (Ferring International Center S.A., Conaris Research Institute AG). In some embodiments, the anti-IL-6 antagonist comprises soluble gp130, FE301 (Conaris/Ferring).

Dosage Regimens: Antibodies, Antigen-Binding Fragments, Peptides. In typical embodiments, antibody, antigen-binding fragments, and peptide IL-6 antagonists are administered parenterally. In some parenteral embodiments, the IL-6 antagonist is administered subcutaneously or intramuscularly. In other parenteral embodiments, the IL-6 antagonist is administered intracerebroventricularly, intracerebrally, intrathecally, or intravenously. In certain intravenous embodiments, the IL-6 antagonist is administered as a bolus. In certain intravenous embodiments, the IL-6 antagonist is administered as an infusion. In certain intravenous embodiments, the IL-6 antagonist is administered as a bolus followed by infusion.

In various embodiments, the antibody, antigen-binding fragment, or peptide IL-6 antagonist is administered in a dose that is independent of patient weight or surface area (flat dose). In some embodiments, the intravenous flat dose is 1 mg, 2 mg, 3 mg, 4 mg, 5 mg, 6 mg, 7 mg, 8 mg, 9 mg, or 10 mg. In some embodiments, the intravenous flat dose is 11 mg, 12 mg, 13 mg, 14 mg, 15 mg, 16 mg, 17 mg, 18 mg, 19 mg, or 20 mg. In some embodiments, the intravenous flat dose is 25 mg, 30 mg, 40 mg, or 50 mg. In some embodiments, the intravenous flat dose is 60 mg, 70 mg, 80 mg, 90 mg, or 100 mg. In some embodiments, the intravenous flat dose is 1-10 mg, 10-15 mg, 15-20 mg, 20-30 mg, 30-40 mg, or 40-50 mg. In some embodiments, the intravenous flat dose is 1-40 mg, or 50-100 mg.

In some embodiments, the subcutaneous flat dose is 10 mg, 20 mg, 30 mg, 40 mg, 50 mg, 60 mg, 70 mg, 80 mg, 90 mg, or 100 mg. In some embodiments, the subcutaneous flat dose is 110 mg, 120 mg, 130 mg, 140 mg, 150 mg, 160 mg, 170 mg, 180 mg, 190 mg, or 200 mg. In some embodiments, the subcutaneous flat dose is 210 mg, 220 mg, 230 mg, 240 mg, or 250 mg. In some embodiments, the subcutaneous flat dose is 10-100 mg, 100-200 mg, or 200-250 mg. In some embodiments, the subcutaneous flat dose is 10-20 mg, 20-30 mg, 30-40 mg, 40-50 mg, 50-60 mg, 60-70 mg, 70-80 mg, 80-90 mg, or 90-100 mg. In some embodiments, the subcutaneous flat dose is 100-125 mg, 125-150 mg, 150-175 mg, 175-200 mg, or 200-250 mg.

In various embodiments, the antibody, antigen-binding fragment, or peptide IL-6 antagonist is administered as a patient weight-based dose.

In some embodiments, the antagonist is administered at a parenteral dose of 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg or 1.0 mg/kg. In some embodiments, the antagonist is administered at a dose of 1.5 mg/kg, 2 mg/kg, 2.5 mg/kg, 3 mg/kg, 3.5 mg/kg, 4 mg/kg, 4.5 mg/kg, or 5 mg/kg.

In some embodiments, the subcutaneous weight-based dose is 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg or 1.0 mg/kg. In some embodiments, the antagonist is administered at a dose of 1.5 mg/kg, 2 mg/kg, 2.5 mg/kg, 3 mg/kg, 3.5 mg/kg, 4 mg/kg, 4.5 mg/kg, or 5 mg/kg.

In various intravenous embodiments, the IL-6 antagonist is administered once every 7 days, once every 14 days, once every 21 days, once every 28 days, or once a month. In various subcutaneous embodiments, the IL-6 antagonist is administered once every 14 days, once every 28 days, once a month, once every two months (every other month), or once every three months.

In some embodiments, the IL-6 antagonist is tocilizumab. In various embodiments, tocilizumab is administered s.c. in a starting dose for patients≥100 kg of 162 mg once every week. In some embodiments, tocilizumab is administered intravenously at a dose of 4 mg/kg once every 4 weeks followed by an increase to 8 mg/kg every 4 weeks based on clinical response.

JAK and STAT Inhibitors. In typical embodiments, small molecule JAK inhibitors and STAT inhibitors are administered orally. In various embodiments, the inhibitor is administered once or twice a day at an oral dose of 1-10 mg, 10-20 mg, 20-30 mg, 30-40 mg, or 40-50 mg. In some embodiments, the inhibitor is administered once or twice a day at a dose of 50-60 mg, 60-70 mg, 70-80 mg, 80-90 mg, or 90-100 mg. In some embodiments, the inhibitor is administered at a dose of 5, 10, 15, 20, 25, 30, 35, 40, 45, or 50 mg PO once or twice a day. In some embodiments, the inhibitor is administered at a dose of 75 mg PO QD or BID, 100 mg PO QD or BID. In certain embodiments, the JAK inhibitor is tofacitinib, and is administered at a dose of 5 mg PO BID or 11 mg PO qDay. In certain embodiments, the JAK inhibitor is decernotinib, and is administered at a dose of 25 mg, 50 mg, 100 mg, or 150 mg PO BID. In certain embodiments, the inhibitor is ruxolitinib, and is administered at dose of 25 mg PO BID, 20 mg PO BID, 15 mg PO BID, 10 mg PO BID, or 5 mg PO BID.

In some embodiments, the anti-IL-6 receptor antibody or the anti-IL-6 antibody, or antigen-binding fragment or derivative of either, has a $K_D$ for binding human IL-6 receptor or human IL-6 of less than 100 nM, less than 50 nM, less than 10 nM, or less than 1 nM. In certain embodiments, the anti-IL-6 receptor antibody or anti-IL-6 antibody, or antigen-binding fragment or derivative of either, has an elimination half-life following systemic administration (e.g., intracerebroventricular, intracerebral, intrathecal, intravenous, or parenteral administration (including subcutaneous and intramuscular modes) of at least 7 days, of at least 14 days, of at least 21 days, or at least 30 days.

"Isolated," as used herein, is intended to refer to an antibody or combination of two, three or four antibodies that is substantially free of other antibodies having different antigenic specificities. In addition, an isolated antibody is typically substantially free of other cellular material and/or chemicals. In one embodiment, a combination of "isolated" monoclonal antibodies having different IL-6 receptor- binding specificities and/or IL-6 binding specificities is combined in a well-defined composition.

An "antigen" is a substance, including peptide determinants of IL-6 receptor, to which an antibody binds.

The term "fragment thereof," as applied to a polypeptide antigen, antibody, or other polypeptide described herein, refers to a peptide or polypeptide comprising any portion of the amino acid sequence of the polypeptide, wherein the fragment substantially retains at least one function of the full-length polypeptide from which it was derived. For example, a fragment can retain at least one physiochemical, physiological, pharmacodynamic, pharmacokinetic or immunological activity of the full-length molecule and/or an ability to be processed, trafficked or secreted in a way similar to the native biologically active molecule from which it was derived. It may contain one or more linear (e.g., about 5-20 residues in length) or conformational B cell epitopes or one or more T cell epitopes which may be MHC Class I (e.g., about 8-11 residues in length) or Class II restricted (e.g., about 13-17 residues in length).

The terms "specific binding," "specifically binds," "selective binding," and "selectively binds," mean that an antibody exhibits appreciable affinity for a particular antigen or epitope and, generally, does not exhibit significant crossreactivity with other antigens and epitopes. "Appreciable" or preferred binding includes binding with a $K_D$ of $10^6$, $10^7$, $10^8$, $10^9$, or $10^{10}$ $M^{-1}$ or better. The $K_D$ or affinity constant of an antibody antigen interaction indicates the concentration of antibody at which 50% of antibody and antigen molecules are bound together. At a particular fixed antigen concentration, 50% of a higher (i.e., stronger) affinity antibody will bind antigen molecules at a lower antibody concentration than would be required to achieve the same percent binding with a lower affinity antibody. Thus a lower $K_D$ value indicates a higher (stronger) affinity.

A "biologically active" or "active" molecule, such as a polypeptide (e.g., antibody or antibody fragment) of interest will exhibit at least one activity of the native molecule, such as an ability to modulate the immune system, treat an autoimmune disease, induce humoral or cellular immunity, interfere with virus replication, treat a tumor or microbial infection, contain diagnostically or immunologically useful epitopes, or any other function of the native molecule. These functions will depend on the nature of the native polypeptide of interest. In some embodiments, an IL-6 antagonist, such as an anti-IL-6 receptor antibody, will be administered with one or more other biologically active compounds, such as STAT3 inhibitors, inhibitors of other inflammatory cytokines, antibiotics such as those that treat brain infections, or anti-inflammatory drugs such as NSAIDS, steroids such as cortisol, that reduce inflammation.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Throughout this specification and the claims which follow, unless the context requires otherwise, the word "comprise", and variations such as "comprises" and "comprising" means various components can be co jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all sub-ranges subsumed therein.

Some non-limiting embodiments of the invention include:

A method for treating hydrocephalus or reducing the risk of acquiring hydrocephalus comprising administering to a subject in need thereof an agent that reduces or blocks binding between interleukin 6 and an IL-6 receptor or otherwise antagonizes the interaction between IL-6 and an IL-6 receptor. Advantageously, this method is directed to treatment of a subject having, at risk of progression of, or at risk of developing multiloculated hydrocephalus, though it may also be performed on subjects having, at risk of progression, or at risk of developing uniloculated hydrocephalus or other forms of hydrocephalus including congenital and acquired hydrocephalus, communicating and non-communicating hydrocephalus, and normal pressure hydrocephalus.

This method may be practiced on subjects of any age and most preferably on those in age groups most susceptible to development of multiloculated hydrocephalus. A subject may be in utero, a neonate, or an infant that is >0, 1, 2, 3, 4, 5, 6, 7, 8, 9, 10, 11 or 12 months old, or 1, 2, 3 or more years of age. Older children, teenagers, young adults and adults may also be treated with the methods described herein.

The method may be performed using an agent that interferes, antagonizes or otherwise blocks or inhibits the interaction of IL-6 with an IL-6 receptor. Advantageously, when the subject is human, the agent will be a humanized antibody or antibody fragment that binds to an IL-6 receptor, such as gp130 or CD126, or to an IL-6 receptor complex. One example of such an antibody is tocilizumab (Actemra). Antibodies that crossblock binding of known anti-IL6 receptor antibodies to IL-6 receptors, such as those crossblocking binding of tocilizumab (Actemra), may also be used. Competing antibodies that recognize the same or an overlapping epitope recognized by another antibody, such as tocilizumab, can be identified using routine techniques such as an immunoassay, for example, by showing the ability of one antibody to block the binding of another antibody to a target antigen, i.e., a competitive binding assay.

Agents, such as humanized antibodies, that bind to IL-6 and attenuate or block IL-6 binding to or activation of an IL-6 receptor may also be used. One example of an antibody that binds to IL-6 is siltuximab (Sylvant). Antibodies that crossblock binding of known anti-IL6 antibodies to IL-6, such as those crossblocking binding of siltuximab (Sylvant), may also be used. Antibodies to IL-6 receptors and to IL-6 may be used in conjunction with each other.

Another embodiment of the invention is directed to a method for preventing, treating, reducing the severity of, or reducing progression of multiloculated hydrocephalus comprising administering to a subject at risk of developing multiloculated hydrocephalus an antibody against an IL-6 receptor. This method may also be applied to treatment of other kinds of hydrocephalus and neurological disorders associated with IL-6 mediated proliferation of brain cells. Advantageously the subject of this method is human and may be in utero or no more than two years of age.

Any antibody that inhibits interaction of IL-6 with its receptor, activation of the receptor, or proliferation of brain cells associated with hydrocephalus, may be used. Advantageously when a human subject is treated a human antibody or a humanized antibody is used, though chimeric antibodies containing human sequences may also be used. This antibody may be polyclonal or monoclonal. Antibodies that crossblock the binding of Tocilziumab to the IL-6 receptor or its activity may be employed. Advantageously, Tocilziumab may be used in the method.

The antibody or antibodies of the invention may be administered by any mode that inhibits proliferation of brain cells or that prevents or reduces the severity of hydrocephalus, including intracerebroventricularly, intracerebrally, intrathecally, intravenously, or parenterally administering the antibody that binds to an IL-6 receptor. In some embodiments, the administration of the antibody will reduce the IL-6 level in the cerebrospinal fluid of the subject compared to the level in a control subject to whom the antibody was not administered. The control subject may be the subject to whom the antibody is later administered, prior to treatment (e.g., the IL-6 level prior to administration of an IL-6 receptor antibody or other IL-6 antagonist).

In one or more embodiments, the antibody to an IL-6 receptor, to IL-6, and/or an agent that inhibits STAT3, described herein may be administered prophylactically (e.g., to prevent or ameliorate pathophysiology of a brain disease or disorder such as multiloculated hydrocephalus), therapeutically (e.g., to treat or to modulate pathophysiology of a brain disease or disorder such as multiloculated hydrocephalus) or both, in a manner compatible with the dosage formulation, and in such an amount and manner as will be prophylactically and/or therapeutically effective.

This method may further comprise administering at least one STAT3 inhibitor and/or administering an antibody that binds to IL-6.

EXAMPLE

Testing the Effect of IL-6 on Proliferation of Brain Cells

Progressive intraventricular septation growth, which comprises fibroglial tissues, is accompanied by brain cell proliferation. The effects of IL-6 on the proliferation of whole brain cells from embryonic rats were evaluated. The results reported below showed that IL-6 induces proliferation of brain cells. This is significant because chronic inflammation is associated with hydrocephalus and cytokines, including IL-6, are increased during chronic inflammation. Thus, an increase in IL-6 during chronic inflammation is consistent with abnormal proliferation of brain cells.

Embryonic rat whole brain at 18 weeks gestation was obtained from a healthy pregnant mother rat. Cells were extracted, mixed with complete PRMI media, and kept in 96 well plate for rest in the incubator for 24 hours.

After that IL-6 was added to each well by serial dilution from concentration of 500 ng/cc to 39.09 pg/cc. Some wells were kept as negative controls and only contained cells without IL-6. Others wells were kept as positive controls and contained cells with a reagent (Phytohaemagglutinin, PHA) that is well known to cause cell proliferation.

Plate was incubated for 72 hours after which cells were taken out of the incubator and Water Soluble Tetrazolium (WST) was added into each well for 3 hours and for 4 hours. The plate was returned back to the incubator.

After 3 and 4 hours, the plate was taken out from the incubator and reading was measured by using spectrophotometer at a wavelength of 450 nanometers. Cell proliferation was measured by spectrophotometer with higher absorptions correlating with higher cell proliferation. For each 96-well plate readings were taken 3 hours and 4 hours after adding WST.

Statistical analysis was used to compare the significance of proliferation between different groups and the effect of the IL-6 on the different groups. Student's t-test two-tailed was used to compare the statistical significance of proliferation between two groups. Whereas, Student's t-test one tailed was used to test the effect of IL-6 on the different groups. P-value was considered significant at (P-value<0.05).

3 hours post WST addition. There was a significance difference in proliferation between negative and positive controls (P=0.04). The highest proliferation was found for cells exposed to 1,000 pg/cc of IL-6, followed by that of cells with an IL-6 concentration of 156 pg/cc, 125 pg/cc, 250 pg/cc and 1250 pg/cc. There was a significant difference in proliferation between negative control cells with all IL-6 concentrations (P<0.05), except for cells with IL-6 concentration of 1,250 p/cc, 2500 pg/cc, 500 pg/cc, 50 ng/cc, and 500 ng/cc.

4 hours post WST addition. There was a significance difference in proliferation between negative and positive controls (P=0.013). The highest cellular proliferation was detected for cells exposed to a concentration of IL-6 of 1,000 pg/cc, followed by cells exposed to an IL-6 concentration of 1250 pg/cc, 156 pg/cc, 312 pg/cc, 250 pg/cc, 625 pg/cc, or 125 pg/cc. There was a significant difference in proliferation between negative control cells with all IL-6 concentrations (P<0.05), except for cells with IL-6 concentration of 1,250 pg/cc, 2,500 pg/cc, 500 pg/cc, 50 ng/cc, and 500 ng/cc.

These results show that IL-6 can cause brain cells to proliferate, in some cases, to a greater degree than PHA-induced proliferation in the positive controls. The highest proliferation was obtained after 72 hours after 4 hours of adding WST; for that reason we choose the proliferation after 72 hours. This supports the pathogenesis mentioned in literature that it is due to chronic inflammation. The highest proliferation was for cells with IL-6 concentration of 1,000 pg/cc. There was a significant difference in the proliferation between negative control and cells with IL-6 concentration of 1,000 pg/cc (P=0.00013). Also, the effect of IL-6 at the above-mentioned concentration 1,000 pg/cc was significant ($P=6.78 \times 10^{-5}$).

After 72 hours the proliferation of cells with IL-6 was more than that of the positive control indicating that IL-6 has a higher effect on cell proliferation than PHA.

These results show that brain cells proliferate in the presence of IL-6 and suggest that blockage of the interaction between IL-6 and IL-6 receptors on brain cells can reduce brain cell proliferation.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

INCORPORATION BY REFERENCE

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The invention claimed is:

1. A method for treating or reducing the severity of septated multiloculated hydrocephalus comprising
administering to a human subject, who is suffering from septated multiloculated hydrocephalus, an antibody that binds to an IL-6 receptor in an amount that reduces proliferation of fibroglial tissue, thereby treating or reducing the severity of septated multiloculated hydrocephalus; wherein said antibody is Tocilizumab.

2. The method of claim 1, wherein the human subject has progressive intraventicular septation growth.

3. The method of claim 1, wherein the antibody is administered intracerebroventricularly, intracerebrally, or intrathecally.

4. The method of claim 1, further comprising administering at least one STAT3 inhibitor or other 1L-6 antagonist; wherein the STAT3 inhibitor is AZD9150 or an antisense polynucleotide to a human STATS polynucleotide; and wherein the other IL-6 antagonist is C326 or FE301.

5. The method of claim 1, further comprising administering a neutralizing antibody that binds to IL-6.

6. The method of claim 1, further comprising contacting brain cells with an NSAID or other anti-inflammatory drug; or cortisol or another steroid.

7. The method of claim 1, wherein the subject is in utero.

8. The method of claim 1, wherein the subject is a neonate or child.

9. The method of claim 1, wherein the subject is an adult.

10. A method for treating or reducing the severity of septated multiloculated hydrocephalus comprising intracerebroventricularly, intracerebrally, or intrathecally administering to a human subject, who is suffering from multiloculated hydrocephalus, an antibody that binds to an IL-6 receptor in an amount that reduces proliferation of fibroglial tissue, thereby treating or reducing the severity of septated multiloculated hydrocephalus;
wherein said antibody is Tocilizumab.

* * * * *